United States Patent [19]

Kraus et al.

[11] Patent Number: 5,880,305
[45] Date of Patent: Mar. 9, 1999

[54] PROCESS FOR PREPARATION OF SIOH-FUNCTIONAL CARBOSILANE DENDRIMERS

[75] Inventors: Harald Kraus, Leverkusen; Markus Mechtel, Köln, both of Germany

[73] Assignee: Bayer AG, Leverkusen, Germany

[21] Appl. No.: 41,378

[22] Filed: Mar. 12, 1998

[30] Foreign Application Priority Data

Mar. 20, 1997 [DE] Germany .................. 197 11 650.7

[51] Int. Cl.$^6$ ..................................... C07F 7/08
[52] U.S. Cl. .................. 556/459; 556/431; 556/435; 528/15; 528/19; 528/21
[58] Field of Search ................... 556/459, 435, 556/431; 528/15, 19, 21

[56] References Cited

U.S. PATENT DOCUMENTS 5,677,410  10/1997  Mager et al. .................... 528/15
5,679,755  10/1997  Mager et al. .................... 556/459 UX
5,739,218  4/1998   Dvornic et al. ................. 556/459 UX

*Primary Examiner*—Paul F. Shaver
*Attorney, Agent, or Firm*—Connolly and Hutz

[57] ABSTRACT

The present invention relates to a process for the preparation of SiOH-functional carbosilane dendrimers.

6 Claims, No Drawings

PROCESS FOR PREPARATION OF SIOH-FUNCTIONAL CARBOSILANE DENDRIMERS

The present invention relates to a process for the preparation of SiOH-functional carbosilane dendrimers.

Dendrimers are strongly branched molecules having a highly ordered, generally three-dimensional, structure and a molar mass within the range of the molar mass of oligomers or polymers.

However, dendrimers have the advantage that they can be tailor-made to have precisely uniform molar mass, while conventional polymers always show a particular distribution of molar masses. Certain functional dendrimers having a defined number of reactive terminal groups can moreover be prepared.

U.S. Pat. No. 5,677,410 and DE-A 19 603 241 which corresponds to copending U.S. Ser. No. 08/785,463 disclose SiOH-functional carbosilane dendrimers. The latter are used, for example, for preparing organic-inorganic hybrid materials and coatings (U.S. Pat. No. 5,677,410), for binding catalytically active metal compounds or as cross-linking agents in condensation-cross-linking organopolysiloxane compositions.

According to U.S. Pat. No. 5,677,410 and DE-A 19 603 241 SiOH-functional carbosilane dendrimers are prepared by reacting the corresponding Si-halogen-functional carbosilane dendrimers with water in the presence of a base in an apolar solvent. Triorganoamines, preferably trialkylamines, are used here as bases, and aliphatic ethers as apolar solvents.

However, a disadvantage of this reaction is the by-product trialkylamine hydro-chloride, which is precipitated as a highly voluminous solid which must then be filtered off in a tedious operation. During the reaction this hinders or prevents the achievement of uniform intermixing of the reaction mixture, such that as a result of concentration gradients and temperature gradients side-reactions are favoured which lead to the formation of oligomers.

The disadvantages mentioned, the laborious nature of the process steps and the extremely low space-time yield therefore mark the process described in U.S. Pat. No. 5,677,410 and DE-A 196 03 241 as extremely unfavourable for industrial preparation of SiOH-functional carbosilane dendrimers.

There was therefore a pressing need to provide a process for the preparation of SiOH-functional carbosilane dendrimers without the known disadvantages of the prior art.

It has now been found that the disadvantages mentioned can be avoided by exploiting the different solubility properties of the product and the by-product.

The present invention therefore provides a process for the preparation of carbosilane dendrimers of the formula (I)

$$K[(CH_2)_nSiX_aR_{3-a}]_i \qquad (I)$$

where n=2–6, preferably n=2, and R=$C_1$–$C_{18}$-alkyl and/or $C_6$–$C_{20}$-aryl, wherein the values n and the radicals R may be the same or different within the molecule, and wherein the further symbols and indices denote the following:

A) K=[$R_{4-i}$Si] where i=3–4, preferably 4 or
B) K=

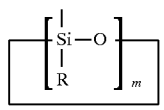

where i=m=3–6, preferably i=m=4 and a) X=(OH) and a=1 or
b) X=[$(CH_2)_nSi(OH)R_2$] and a=1–3, preferably a=3 or
c) X=[$(CH_2)_nSiR_{3-a}[(CH_2)_nSi(OH)R_2]_a$] and a=1–3, preferably a=3 or
d) X=[$(CH_2)_nSiR_{3-a}[(CH_2)_nSiR_{3-a}[(CH_2)_nSi(OH)R_2]_a]_a$] and a=1–3, preferably a=3 by reacting carbosilane dendrimers of the formula (II)

$$K[(CH_2)_nSiY_aR_{3-a}]_i \qquad (II)$$

where n=2–6, preferably n=2, and R=$C_1$–$C_{18}$-alkyl and/or $C_6$–$C_{20}$-aryl, wherein the values n and the radicals R may be the same or different within the molecule, and wherein the further symbols and indices denote the following:

A) K=[$R_{4-i}$Si] where i=3–4, preferably 4 or
B) K=

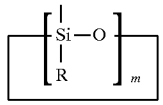

where i=m=3–6, preferably i=m=4 and
a) Y=Cl, Br,I and a=1 or
b) Y=[$(CH_2)_nSi(Z)R_2$] where Z=Cl, Br, I and a=1–3, preferably a=3 or
c) Y=[$(CH_2)_nSiR_{3-a}[(CH_2)_nSi(Z)R_2]_a$] where Z=Cl, Br, I and a=1–3, preferably a=3 or
d) Y=[$(CH_2)_nSiR_{3-a}[(CH_2)_nSiR_{3-a}[(CH_2)_nSi(Z)R_2]_a]_a$] where Z=Cl, Br, I and a=1–3, preferably a=3 with water in the presence of a base or a base mixture and an organic solvent, followed by the addition of organic solvent and water in a ratio by weight of from 0. 5 to 1.4, preferably 0.9 to 1.1.

The reaction is consequently carried out as a two-phase reaction, that is to say the hydrolysis takes place at the phase interface of a two-phase mixture comprising an organic phase in which both the Si-halogen-containing carbosilane dendrimers of the formula (II) (educts) and the SiOH-functional carbosilane dendrimers of the formula (I) (products) dissolve, and an aqueous phase in which the base and the salt formed during the reaction are dissolved.

Any organic solvents and/or solvent mixtures which are not completely water-miscible are considered as solvents of the organic phase within the meaning of the invention. The solvent mixture may optionally be single-phase or multi-phase. Aliphatic ethers are preferably used, particularly preferably tert.-butyl methyl ether.

Any water-soluble bases and mixtures thereof, such as, for example, NH3, alkali metal hydroxides, and ammonium and alkali metal carbonates, hydrogen carbonates, phosphates, hydrogen phosphates and/or acetates, may be used as bases within the meaning of the invention. NH$_3$, alkali metal hydroxides, alkali metal carbonates and/or alkali metal hydrogen carbonates, are preferably used, particularly preferably NH3.

The bases are preferably used in a stoichiometric quantity or in an excess, in relation to the quantity of acid liberated by the hydrolysis, preferably in a two- to ten-fold excess if NH$_3$ is the base.

The process according to the invention is preferably carried out at temperatures of ≧0° C., particularly preferably between 0° C. and 50° C.

The compounds of the formula (II) may preferably be prepared according to U.S. Pat. No. 5,677,410 and DE-A 196 03 241 which corresponds to copending U.S. Ser. No.

08/785,463 by hydrosilylation reactions, that is to say by reacting suitable unsaturated silanes with hydridosilanes such as, for example, halosilanes, in the presence of a catalyst.

In a particularly preferred embodiment of the invention the carbosilane dendrimers of the formula (II) are prepared by reacting unsaturated silanes such as, for example, tetravinyl silane and cyclo[tetra(methylvinyl siloxane)], with halohydridosilanes such as, for example, chlorodimethyl silane in the presence of homogeneous catalysts, preferably platinum complexes in a vinyl group-containing siloxane matrix, such as, for example, Silopren U catalyst Pt/S, a 68% solution in isopropanol of a Pt complex substituted with cyclo[tetra(methylvinyl siloxane)] ligands.

If the hydrosilylation has been carried out previously in a solvent which is suitable for the process according to the invention, the reaction product formed in that process may also be used in situ, that is to say without further working-up.

The process according to the invention may be carried out both batch-wise, for example in a stirred tank reactor, and in continuous manner, for example in a tubular-flow reactor. For this, the carbosilane dendrimer of the formula (II) which is dissolved in a suitable solvent, preferably an aliphatic ether, particularly preferably tert.-butyl-methyl ether, or optionally the reaction product of the hydrosilylation reaction is preferably added slowly to the two-phase mixture, wherein the aqueous and the organic phase preferably become intensively intermixed. The latter intermixing may, for example, take place in the stirred tank reactor as a result of intensive stirring or in the tubular-flow reactor as a result of turbulent flow.

The intermixing causes the reaction at the phase interface to be favoured. The acid liberated in the hydrolysis reacts with the base or base mixture to give a salt or salt mixture, which dissolves in the aqueous phase. The SiOH-finctional carbosilane dendrimer of the formula (I) which is formed dissolves in the organic phase. Because of the different solubility properties of the reaction components and the avoidance of precipitate formation, the product can be separated and worked up in simple manner.

After the reaction is complete, the phases are separated, optionally batch-wise in a separate reaction vessel if the reaction has been continuous.

The aqueous phase is preferably separated, and the organic phase is washed once or more with water or an aqueous solution of a salt, a base or an acid, as necessary, after which traces of water are removed, for example by drying over anhydrous alkali metal sulphates, alkaline earth metal sulphates, calcium chloride and/or molecular sieves or by distillation processes.

The SiOH-functional carbosilane dendrimer of the formula (I) which is formed may be isolated by removing the volatile constituents, for example by condensation or distillation, wherein it arises as a solid or an oil. If the product is a solid it may also be isolated in direct manner by dispensing the organic phase dropwise into a solvent (precipitant) or solvent mixture in which the product is insoluble or only slightly soluble, followed by filtering. Suitable solvents are, for example, cyclic, aliphatic or aromatic hydrocarbons such as, for example, cyclohexane, pentane, hexane, heptane, toluene and/or xylene. It is also possible to add the precipitant to the organic phase.

If the product is to be reacted further in dissolved form or supplied thus to an application, the isolation of the product may be omitted, and the organic phase may be used in direct manner. Other working-up steps are also possible, for example solvent exchange by the addition of a preferably higher-boiling solvent, followed by distillation or condensation to remove the original solvent or solvent mixture.

The process according to the invention is explained by the Examples which follow, while not, however, being restricted to the latter.

EMBODIMENT EXAMPLES

Note

With the exception of the working-up steps which follow the hydrolysis, all reactions are carried out under a protective gas (argon) atmosphere.

Tert.-butylmethyl ether (hereinbelow abbreviated to TBME) ($H_2O$ content<0.05%), n-hexane, diethyl ether, tetravinyl silane, cyclo[tetra(methyl vinyl siloxane)], chlorodimethyl silane, $NaHCO_3$, $Na_2CO_3$, NaOH, NaCl and $Na_2SO_4$ were used in direct manner as commercial products without further working-up. The aqueous NH3 solutions were prepared by dilution of a 25% aqueous $NH_3$ solution.

The heterogeneous catalyst 1 (Pt content 1%) was prepared in accordance with Example 8 of U.S. Pat. No. 5,677,410 by coating pulverulent activated carbon with $H_2PtCl_6$.

The Silopren U catalyst Pt/S (a 68% solution in isopropanol of a Pt complex substituted with cyclo[tetra (methylvinyl siloxane)] ligands) was obtained from Bayer AG (Germany). $^1$H-NMR measurements were taken at 400 MHz.

Example 1

Preparation of the starting compound $Si[(CH_2)_2Si(CH_3)_2Cl]_4$

The synthesis was as described in U.S. Pat. No. 5,677,410:

Under argon, 234.2 g (2.475 mol) chlorodimethyl silane, 500 ml TBME and 1.5 g catalyst 1 were added to 75 g (0.550 mol) tetravinyl silane. The reaction mixture was heated, with vigorous stirring, to 45° C. until an exothermic reaction set in and the temperature rose to 51° C. A mixture comprising 525 g (3.853 mol) tetravinyl silane, 1639.4 g (17.327 mol) chlorodimethyl silane and 940 ml TBME was then added slowly dropwise, wherein care was taken that the reaction temperature did not fall below 50° C. Stirring was then continued for 1.5 hours under reflux, the reaction mixture was cooled to room temperature, the catalyst was filtered off over a frit, and volatile constituents were removed from the colourless solution under vacuum. The product took the form of a white solid. Yield: 2120.8 g (94% of theoretical yield).

Example 2

Synthesis of $Si[(CH_2)_2Si(CH_3)_2OH]_4$ using $NH_3$ as the base

In a 10-liter flat-flange vessel with a discharge cock 2.6 liter (1924 g) TBME and 2894 g of an aqueous $NH_3$ solution containing 473.5 g (27.8 mol) $NH_3$ were placed under argon. With vigorous stirring which caused intensive intermixing of the two phases, 720 g (1.399 mol) $Si[(CH_2)_2Si(CH_3)_2Cl]_4$ (from Example 1) were added slowly dropwise to 800 ml (592 g) dried TBME, wherein the reaction temperature rose slowly to 38° C. Following the dropwise addition, stirring was continued for 1.5 hours at room temperature, after which the phases were separated, the organic phase was washed twice with 3 liters water in each case and was dried over $Na_2SO_4$. After the drying agent had been filtered off, the organic phase was added dropwise to 10 liters n-hexane, wherein the product was precipitated as a finely crystalline white solid, which was filtered off and dried under vacuum at 30° C. (ratio by weight of $TBME/H_2O$: 1.04) Yield: 464.7 g (75.4% of theoretical yield). $C_{16}H_{44}O_4Si_5$ M=440.95 g/mol M.p. 142°–143° C. $^1$H-NMR (DMSO-$d_6$):=0.0 ppm (s, 6H, $Si(CH_3)$); 0.38 ppm (m, 4H, $Si(CH_2)_2Si$); 5.22 ppm (s, 1H, Si(OH)).

Example 3

Synthesis of $Si[(CH_2)_2Si(CH_3)_2OH]_4$ using $NaHCO_3$ as the base 10 g (19.4 mmol) $Si[(CH_2)_2Si(CH_3)_2Cl]_4$ (from Example 1) dissolved in 50 ml (37 g) TBME were added slowly dropwise at room temperature to an intensively stirred mixture comprising a solution of 16.38 g (195 mmol) $NaHCO_3$ in 200 ml $H_2O$ and 200 ml (148 g) TBME, wherein the temperature rose to 28° C. Stirring was then continued for 1 hour, and the organic phase was separated in a separatory funnel and dried over $Na_2SO_4$. After the drying agent had been filtered off, the organic phase was added dropwise to 1 liter n-hexane, wherein the product precipitated out as a finely crystalline white solid, which was filtered off and dried under vacuum at 30° C. (ratio by weight of $TBME/H_2O$: 0.93) Yield: 5.2 g (60.7% of theoretical yield) M.p. 141°–142° C.

Example 4

Synthesis of $Si[(CH_2)_2Si(CH_3)_2OH]_4$ using $Na_2CO_3$ as the base 30.94 g (292 mmol) $Na_2CO_3$ in 1000 ml $H_2O$ and 1000 ml (740 g) TBME were taken at room temperature, and 50 g (97.1 mmol) $Si[(CH_2)_2Si(CH_3)_2Cl]_4$ (from Example 1) in 250 ml (185 g) TBME were added dropwise to the intensively stirred mixture, under argon. Stirring was then continued for 1 hour, and the organic phase was separated, dried over $Na_2SO_4$ and then added dropwise to 5 liters n-hexane, wherein the product precipitated out as a finely crystalline white solid, which was filtered off and dried under vacuum at 30° C. (ratio by weight of $TBME/H_2O$: 0.93) Yield: 33.1 g (77.3% of theoretical yield) M.p. 142°–143° C.

Example 5

Synthesis of $Si[(CH_2)_2Si(CH_3)_2OH]_4$ using $Na_2CO_3$ and NaOH as the base 10 g (19.4 mmol) $Si[(CH_2)_2Si(CH_3)_2Cl]_4$ (from Example 1) dissolved in 50 ml (37 g) TBME were added dropwise under argon at room temperature to an intensively stirred mixture comprising a solution of 2.34 g (58.5 mmol) NaOH and 1.55 g (14.6 mmol) $Na_2CO_3$ in 200 ml $H_2O$ and 200 ml (148 g) TBME, stirring continued for 1 hour, and the organic phase was separated, dried over $Na_2SO_4$ and added dropwise to 1000 ml n-hexane, wherein the product precipitated out as a white solid. The latter was filtered off and dried at 70° C. Yield: 6.3 g (73.5% of theoretical yield) (ratio by weight of $TBME/H_2O$: 0.93) M.p. 141°–142° C.

Example 6

Synthesis of $Si[(CH_2)_2Si(CH_3)_2OH]_4$ using $NH_3$ as the base 200 g (1.468 mol) tetravinyl silane, 480 ml (355.2 g) TBME and 0.1 ml Silopren U catalyst Pt/S were placed under a protective gas atmosphere, and a total of 556 g (5.876 mol) $(CH_3)_2SiHCl$ were added dropwise, with stirring. In order to initiate the reaction, approximately 30 ml $(CH_3)_2SiHCl$ were first added rapidly at room temperature, wherein the temperature rose to approximately 32° C. as a result of the exothermic reaction which set in. The residue of the $(CH_3)_2SiHCl$ was added dropwise at a rate such that the temperature rose continuously to approximately 60° C. Heating was then continued for 2 hours under reflux. The reaction mixture, when cooled to room temperature, was diluted with 300 ml (222 g) TBME and was added dropwise within 1.5 hours to an intensively stirred mixture comprising 473.5 g (27.8 mol) $NH_3$ in 2900 ml $H_2O$ and 2600 ml (1924 g) TBME. Stirring was then continued for 1 hour, the aqueous phase was separated, and the organic phase was washed twice, each time with 1000 ml $H_2O$, and then dried over $Na_2SO_4$. After the drying agent had been filtered off, the organic phase was added dropwise to 10 liters n-hexane, wherein the product precipitated out as a white solid, which was filtered off and dried under vacuum at 30° C. (ratio by weight of $TBME/H_2O$: 0.86) Yield: 359 g (55.5% of theoretical yield, in relation to tetravinyl silane) M.p. 141°–143° C.

Example 7

Synthesis of $Si[(CH_2)_2Si(CH_3)_2OH]_4$ using $NH_3$ as the base

A mixture of 25 g (183 mmol) tetravinyl silane and 69.9 g (739 mmol) $(CH_3)_2SiHCl$ was added dropwise to a starting charge of 170 ml (125.8 g) TBME and 0.05 ml Silopren U catalyst Pt/S, under a protective gas atmosphere and with heating to reflux. Stirring was then continued for 1 hour under reflux, and the reaction mixture was cooled to room temperature and added dropwise to an intensively stirred mixture comprising 430 ml (318.2 g) TBME and 400 g of an aqueous solution containing 60.8 g (3.576 mol) $NH_3$. Stirring was then continued for 1 hour, following which the aqueous phase was separated, and the organic phase was washed once each with 400 ml $H_2O$ and 400 ml of a concentrated aqueous NaCl solution, dried over $Na_2SO_4$ and added dropwise to 1100 ml n-hexane. The solid which precipitated out was filtered off and dried under vacuum at 30° C. (ratio by weight of $TBME/H_2O$: 1.31) Yield: 54.8 g (67.8% of theoretical yield, in relation to tetravinyl silane) M.p. 142°–143° C.

Example 8

Synthesis of cyclo-$\{OSi(CH_3)[(CH_2)_2Si(CH_3)_2(OH)]\}_4$ using $NH_3$ as the base 788 g (8.33 mol) $(CH_3)_2SiHCl$ were added dropwise at 45° C., with stirring, to a mixture comprising 689 g (2 mol) cyclo-$\{OSi(CH_3)(C_2H_3)\}_4$, 1200 ml (888 g) TBME and 0.2 ml Silopren U catalyst Pt/S. The reaction temperature rose continuously to 60° C. during this addition. After the addition was complete, heating was continued under reflux for 1 hour, and the reaction mixture was cooled to room temperature and added slowly dropwise to an intensively stirred two-phase mixture comprising 3000 ml (2220 g) TBME and 3750 g of an aqueous $NH_3$ solution which contained 681 g (40 mol) $NH_3$. Stirring was then continued for 1 hour at room temperature, the phases were separated, and the organic phase was washed once each with 3500 ml $H_2O$ and 3500 ml of an approximately 5% NaCl solution and dried over $Na_2SO_4$.

After the drying agent was filtered off, volatile constituents were condensed out under vacuum at 25° C. A clear, slightly yellow-tinged highly viscous oil was obtained which still contained approximately 5% TBME. (ratio by weight of TBME/H$_2$O: 1.01) Yield: 1294 g oil (theoretical yield: 1296.4 g) $^1$H-NMR (DMSO-d$_6$):=0.0 ppm (s$_3$ 6H, Si(CH$_3$)$_2$); 0.08 ppm (s, 3H, Si(CH$_3$)); 0.43 ppm (m, 4H, Si(CH$_2$)$_2$Si); 5.25 ppm (s, 1H, Si(OH)).

Comparative Example 1

(in accordance with U.S. Pat. No. 5,677,410)

Synthesis of Si[(CH$_2$)$_2$Si(CH$_3$)$_2$OH]$_4$ 94.3 g (183.4 mmol) Si[(CH$_2$)$_2$Si(CH$_3$)$_2$Cl]$_4$ were dissolved in 100 ml (70.8 g) diethyl ether (Et$_2$O) and were added dropwise at room temperature to a solution of 110.3 ml (729.3 mmol) triethylamine, 15.3 g (850 mmol) H$_2$O and 3630 ml (2686.2 g) TBME, with vigorous stirring. Triethylamine hydrochloride formed and precipitated out immediately as a voluminous white precipitate. The dropwise addition took place rapidly such that the reaction temperature was between 25° C. and 30° C. After the addition was complete, stirring was continued for 1 hour, and the precipitate was filtered off over a frit which was washed twice, each time with 500 ml TBME. After the volatile constituents had been removed under vacuum at approximately 35° C., the crude product was obtained from the filtrate as a white solid. This was dissolved in 120 ml THF and was added dropwise to 3 liters hexane, with vigorous stirring. The fine white precipitate thus obtained was filtered off, washed with hexane and then dried under vacuum. (ratio by weight of (TBME+Et$_2$O)/H$_2$O: 180.2) Yield: 40.5 g (50.2% of theoretical yield) M.p. 139°–141° C.

Comparative Example 2

Synthesis of the starting product cyclo-{SiO(CH$_3$)[(CH$_2$)$_2$SiCl(CH$_3$)$_2$]}$_4$ (analogous to that of example 6 in DE-A 19603241 which corresponds to copending U.S. Ser. No. 08/785463)

69 g (726.7 mmol) of chlorodimethylsilane and 800 mg of the catalyst Cat 1 were introduced into 50 g (145.2 mmol) of cyclo-{SiO(CH$_3$)(C$_2$H$_3$)}$_4$ in 120 ml of THF with stirring. The reaction mixture was heated to 50° C., no evolution of heat being observed even after 2 hours at this temperature. After a further 20 hours at 55° to 60° C. the mixture was cooled to room temperature and the catalyst was filtered through a reversible frit. The transparent colourless filtrate was freed in vacuo from volatile constituents and the product was obtained in the form of a colourless oil.

Synthesis of cyclo-{OSi(CH$_3$)[(CH$_2$)$_2$Si(CH$_3$)$_2$(OH)]}$_4$ 105 g (145.2 mmol) cyclo-{OSi(CH$_3$)[(CH$_2$)$_2$SiCl (CH$_3$)$_2$)]}$_4$ (prepared as described above) in 100 ml (70.8 g) diethyl ether (Et$_2$O) were added dropwise within one hour to a mixture comprising 87.4 ml (63.6 g; 628.3 mmol) triethylamine, 12.1 ml (12.1 g; 672.2 mmol) H$_2$O and 2850 ml (2109 g) TBME. After the addition was complete, stirring was continued for an hour, after which the voluminous triethylamine hydrochloride precipitate was filtered off. After the precipitate had been washed twice with 400 ml TBME in each case, the volatile constituents were removed under vacuum by rotary film evaporator, and the oily residue was absorbed in approximately 50 ml THF and filtered over silica gel. After removal once more of all the volatile constituents under vacuum, the product was obtained as a viscous oil. (ratio by weight of (TBME+Et$_2$O)/H$_2$O: 180.1) Yield: 64.3 g oil (theoretical yield: 94.1 g)

We claim:

1. A process for the preparation of carbosilane dendrimers of the formula (I)

wherein n=2–6 and R=C$_1$–C$_{18}$-alkyl and/or C$_6$–C$_{20}$-aryl, wherein the values n and the radicals R may be the same or different within the molecule, and wherein the further symbols and indices denote the following:

A) K=[R$_{4-i}$Si] where i=3–4 or

B) K=

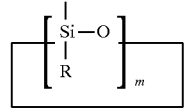

where i=m=3–6 and a) X=(OH) and a=1 or
b) X=[(CH$_2$)$_n$Si(OH)R$_2$] and a=1–3 or
c) X=[(CH$_2$)$_n$SiR$_{3-a}$[(CH$_2$)$_n$Si(OH)R$_2$]$_a$] and a=1–3 or
d) X=[(CH$_2$)$_n$SiR$_{3-a}$[(CH$_2$)$_2$SiR$_{3-a}$[(CH)$_2$Si(OH)R$_2$]$_a$]$_a$] and a=1–3 which comprises reacting carbosilane dendrimers of the formula

wherein n=2–6 and R=C$_1$–C$_{18}$-alkyl and/or C$_6$–C$_{20}$-aryl, wherein the values n and the radicals R may be the same or different within the molecule, and wherein the further symbols and indices denote the following:

A) K=[R$_{4-i}$Si] where i=3–4 or

B) K=

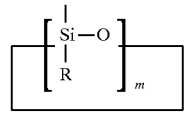

where i=m=3–6 and a) Y=Cl,Br,I and a=1 or
b) Y=[(CH$_2$)$_n$Si(Z)R$_2$] where Z=Cl,Br,I and a=1–3 or
c) Y=[(CH$_2$)$_n$SiR$_{3-a}$[(CH$_2$)$_n$Si(Z)R$_2$]$_a$] where Z=Cl,Br,I and a=1–3
d) Y=[(CH$_2$)$_n$SiR$_{3-a}$[(CH$_2$)$_n$SiR$_{3-a}$[(CH$_2$)$_n$Si(Z)R$_2$]$_a$]$_a$] where Z=Cl, Br, I and a=1–3 with water in the presence of a base, wherein the base is selected from the group consisting of NH$_3$ alkali metal hydroxides, ammonium and alkali metal carbonates, hydrogen carbonates, phosphates, hydrogen phosphates and/or acetates, or a base mixture, and an organic solvent, wherein the organic solvent and water are used in a ratio by weight of from 0.5 to 1.4.

2. A process according to claim 1, wherein the organic solvent is an aliphatic ether.

3. A process according to claim 1, wherein the carbosilane dendrimer of the formula (II) has been prepared by reacting unsaturated silanes with halohydridosilanes in the presence of homogeneous catalysts.

4. A process according to claim 3, wherein the homogeneous catalyst comprises a platinum complex in a vinyl group—containing siloxane matrix.

5. A process for preparing an Si-OH functional carbosilane dendrimer from a corresponding Si-halogen functional carbosilane dendrimer, which process comprises reacting an Si-halogen functional carbosilane dendrimer with water in the presence of a base, wherein the base is selected from the group consisting of $NH_3$ alkali metal hydroxides, ammonium and alkali metal carbonates, hydrogen carbonates, phosphates, hydrogen phosphates and/or acetates, or base mixture followed by addition of organic solvent and water in a ratio by weight of from 0.8 to 1.4.

6. A process according to claim 5, wherein the organic solvent and water are added in a weight ratio of 0.9 to 1.1.

* * * * *